(12) United States Patent
Randive et al.

(10) Patent No.: US 8,524,199 B2
(45) Date of Patent: Sep. 3, 2013

(54) TOOTHPASTE COMPOSITION

(75) Inventors: Vinayak B. Randive, Thane (IN); Vijay K. Gadkari, Mumbai (IN)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 13/388,600

(22) PCT Filed: Aug. 6, 2010

(86) PCT No.: PCT/US2010/044742
§ 371 (c)(1),
(2), (4) Date: Apr. 10, 2012

(87) PCT Pub. No.: WO2011/017633
PCT Pub. Date: Feb. 10, 2011

(65) Prior Publication Data
US 2012/0189561 A1    Jul. 26, 2012

(30) Foreign Application Priority Data

Aug. 7, 2009  (IN) .................... 1643/DEL/2009
Aug. 7, 2009  (IN) .................... 1644/DEL/2009

(51) Int. Cl.
*A61K 8/00*     (2006.01)
*A61K 31/731*   (2006.01)
*A61Q 11/00*    (2006.01)

(52) U.S. Cl.
USPC ............. 424/49; 424/401; 424/76.3; 516/107

(58) Field of Classification Search
USPC ..................... 424/49, 401, 76.3; 516/107
See application file for complete search history.

(56) References Cited

U.S. PATENT DOCUMENTS

| 4,353,890 | A   |   | 10/1982 | Scott          |         |
|-----------|-----|---|---------|----------------|---------|
| 4,702,905 | A   | * | 10/1987 | Mitchell et al.| 424/57  |
| 5,505,933 | A   |   | 4/1996  | Norfleet et al.|         |
| 6,387,354 | B1  |   | 5/2002  | Bixler et al.  |         |
| 7,018,635 | B2  |   | 3/2006  | Tsai et al.    |         |
| 7,189,843 | B2  | * | 3/2007  | Tsai et al.    | 536/114 |
| 2007/0183991 | A1 |  | 8/2007  | Katou et al.   |         |

FOREIGN PATENT DOCUMENTS

JP    10-25302 A    1/1999

OTHER PUBLICATIONS

Notification of Transmittal of the International Search Report and The Written Opinion of the International Searching Authority, or the Declaration, International Application No. PCT/US2010/004742, filing Date Aug. 6, 2010.

* cited by examiner

*Primary Examiner* — Lezah Roberts
(74) *Attorney, Agent, or Firm* — FMC Corporation

(57) ABSTRACT

The present invention is directed to a toothpaste composition comprising a binder, an abrasive, a foaming agent, water, and polyethylene glycol, wherein the binder comprises semi-refined carrageenan. The toothpaste composition has improved shelf life.

6 Claims, No Drawings

TOOTHPASTE COMPOSITION

FIELD OF THE INVENTION

The present invention is directed to a toothpaste composition comprising a binder, an abrasive, a foaming agent, water, and polyethylene glycol, wherein the binder composition comprises semi-refined carrageenan.

BACKGROUND OF THE INVENTION

Carrageenan is a complex mixture of sulfated polysaccharides comprising linear polymers of 1→3 linked [α]-D-galactose units and 1→4 linked [β]-D-galactose units. Carrageenan is produced by red seaweeds where it functions as the principle structural polysaccharide. It is located within the cell wall and intracellular matrix of the plant tissue. The carrageenan content of commercially harvested seaweeds is generally between 30% and 80% based on the seaweed dry weight. Carrageenan finds wide applicability as a food ingredient and is functional in foods such as dairy products, water dessert gels, meat products, confections, beverages, dressings and other such products. Carrageenan is also useful in products such as cosmetics, toothpaste and other personal care products, in soft gel capsules, and in other industrial, medical, pharmaceutical, and agricultural applications. The molecular weight of carrageenan products is typically from about 100,000 to about 1,000,000 Daltons. Carrageenans have the ability to form an almost infinite variety of gels at room temperature with a variety of gelling and melting points. Carrageenan solutions can thicken, suspend, and stabilize particulates, colloidal dispersions and water/oil emulsions. The solutions shear thin, which allows them to be pumped easily. Also, the sheared solutions rapidly rebuild viscosity and suspending power upon standing. Depending upon the application, carrageenans present in parts per million up to a few percent by weight provide gelling, thickening, suspending, binding and/or generates a desired product feel or texture.

Carrageenan is generally soluble in warm water, in which it forms a viscous solution. It is insoluble in most organic solvents and typically forms complexes with proteins. The major types of carrageenan are designated as Kappa, Iota, Lambda, Nu and Mu. These are differentiated based on the nature of the repeating galactose units contained in the carrageenan. The polymer chain can be cleaved by hydrolytic depolymerization upon treatment with an acid or by oxidative depolymerization upon treatment with hydrogen peroxide.

In a typical process for producing refined carrageenan, crude seaweed is first washed with cold water or seawater to remove sand and other particles that may be present after seaweed has been harvested. Carrageenan typically does not swell during the cold wash, primarily because carrageenan in seaweed is associated with structural components of the seaweed, generally cellulose. Depending upon the seaweed species, following the cold wash, a hot water extraction process is typically performed in which the extracted carrageenan is treated with an aqueous base at high temperature. Generally, the base used is an alkali or alkaline earth metal hydroxide such as, for example, sodium hydroxide, calcium hydroxide, or potassium hydroxide. This high temperature aqueous base modification step leads to the formation of 3,6-anhydro linkages in the galactose units of the carrageenan. After this modification, the hot extract is filtered to remove insoluble materials such as cellulose, hemicelluloses and other particulates and acid is added to adjust the pH to 7.5 to 10.5. The filtrate can then be concentrated to about 4% carrageenan for further processing. Optional process steps after extraction include centrifugation and bleaching. Refined carrageenan is typically obtained by precipitation of the extract from the aqueous solution with potassium chloride or an alcohol such as isopropyl alcohol. The resulting carrageenan product is subsequently dried and ground.

Material throughput for production of refined carrageenan on a commercial scale is rate limited. After the extraction step, a hot aqueous stream can typically only contain low concentrations of carrageenan, typically up to about 4%. At higher concentrations of carrageenan, the aqueous stream becomes too viscous to process efficiently.

There has been an ongoing search for more cost-effective methods of preparing semi-refined carrageenan and other carrageenan products as lower cost replacements for conventional carrageenan. Semi-refined carrageenan (SRC) products are those in which few or none of the structural components of the seaweed, principally cellulose, have been removed. During production of SRC, a salt such as potassium chloride or sodium chloride is added during the base modification along with the base. The presence of sufficient amounts of salt prevents disintegration of the seaweed structure and inhibits extraction of carrageenan from the seaweed. An alcohol such as isopropyl alcohol can also be used alone or in combination with salt to inhibit extraction of the carrageenan. Following the base modification step, with the seaweed structure still intact, the processed seaweed is typically dried to afford SRC. When the seaweed is a member of the Euchema family, the SRC obtained is known as processed *Euchema* seaweed (PES).

U.S. Pat. No. 5,801,240 to Rideout et al. discloses a method for producing semi-refined kappa carrageenan. It describes the conventional PES production process with improvements including better monitoring of oxidation-reduction potential of the potassium hydroxide (KOH) solution used in the extraction method and optionally chopping the seaweed prior to KOH cooking. U.S. Pat. No. 5,777,102 to Larsen discloses a modified carrageenan made by partially hydrating seaweed in water/solvent/base mixture to get modification of the carrageenan following which the material is extruded. U.S. Pat. No. 5,502,179 to Larsen discloses a method in which seaweed is reacted under heating in a solvent/water/base mixture to get fully modified carrageenan followed by extrusion to obtain a product with a specific light transmission and Brabender profile. WO 03/059956 to Therkelsen discloses a heterogeneous carrageenan manufacturing process from mono-component seaweed with reduced use level of KOH. This is an improved cost effective method of making carrageenan extract or PES that uses high salt level in combination with NaOH to reduce the level of costly KOH. U.S. Pat. Nos. 6,479,649 B1, 7,018,635 B2, and 7,189,843 B2 to Tsai et al. disclose a method for production of carrageenan and carrageenan products with its main focus on extrusion of seaweed feedstock. U.S. Pat. No. 6,387,354 B1 to Bixler et al. discloses a binder for a toothpaste composition comprising semi-refined kappa and/or semi-refined iota carrageenans in combination with other binder components. Japanese Patent Publication No. JP8005921B2 discloses a modified iota carrageenan having a viscosity of 5 cP to 40 cP in a 1.5% aqueous solution at 75° C. In this disclosure, a part of iota carrageenan can be replaced by lambda carrageenan for a ratio of iota to lambda carrageenan that is 1 to 4 or higher. A mixture of these carrageenans in such a ratio when used as a binder exhibits an effect of stabilizing the quality of toothpaste nearly the same as obtained when iota carrageenan is used alone. Japanese Patent Publication No JP2752610B2 discloses a modified iota carrageenan with a viscosity of 5 cP to 40 cP at 75° C. obtained from *Euchema spinosum* by hydrolyzing its extract with alkali hydrolysis, acid hydrolysis, hydrolysis using an oxidant, or hydrolysis with an enzyme or other microorganisms. When used as a stabilizer in toothpaste formulations, this modified iota carrageenan is preferably compounded with materials like calcium phosphate, glycerol etc. Japanese Patent Publication No. JP2752611B2 discloses toothpaste comprising lambda carrageenan and modified carrageenan the aqueous 1.5% solution of which has a viscosity of 5 cP to 40 cP at 75° C.

Refined carrageenans have some advantages to SRC obtained from the same seaweeds. Refined carrageenans typically hydrate, i.e. begin to swell and become soluble, at lower temperatures than SRC. Another advantage of refined carrageenans is that because SRC contains cellulosics and other materials which are absent in refined carrageenans, gels formed from SRC have a lower clarity compared to gels prepared from refined carrageenan products. Certain semi-refined carrageenans have also experienced stability issues in toothpastes. There remains a continued need for development of a toothpaste having acceptable and/or improved shelf life and stability using semi-refined carrageenan as a replacement for some or all of the refined carrageenan.

SUMMARY OF THE INVENTION

The present invention is directed to a toothpaste composition comprising a binder, an abrasive, a foaming agent, water, and polyethylene glycol, wherein the binder comprises semi-refined carrageenan. The toothpaste composition has improved shelf life.

DETAILED DESCRIPTION OF THE INVENTION

Applicants have found that polyethylene glycol improves the shelf life and stability of a toothpaste composition comprising semi-refined carrageenans. A typical amount of polyethylene glycol for such purpose would be from 1 to 5 wt % of polyethylene glycol by weight of the toothpaste composition, more particularly, 2 wt %, 3 wt %, and 4%. Typical polyethylene glycols useful in the invention include those having an average molecular weight of between 150 to 650 such as those having an average molecular weight of between 190 to 210 (e.g., PEG 200); an average molecular weight of between 285 to 315 (e.g., PEG 300); an average molecular weight of between 380 to 420 (e.g., PEG 400); and an average molecular weight of between 570 to 630 (e.g., PEG 600).

The semi-refined carrageenan of the invention may be an iota carrageenan. An example is a semi-refined, alkali treated iota carrageenan from Euchema seaweed in which all or part of the cellulosics are retained. An alkali treated iota carrageenan product, as used herein, means using an alkali to process the seaweed, which results in an iota carrageenan with a level of 3,6 anhydro galactose that is higher than in its native or natural form. The alkaline treatment converts nu carrageenan (which is present in the seaweed) to iota carrageenan, which is also present in the seaweed. The resulting iota carrageenan comprises about 76 to 100 mol % iota carrageenan. In its native or natural form, iota carrageenan is generally in the range of from 70-75 mol % iota carrageenan. As used herein, the alkali processed seaweed contains iota carrageenan in the range of 76-100 mol % iota. Methods for making such a semi-refined alkali treated iota carrageenan comprise wet treatment steps to produce the semi-refined, alkali treated iota carrageenan followed by drying and grinding. Wet treatment steps include washing the seaweed, treating the seaweed with a base, such as sodium hydroxide, at a temperature from about 25° C. to about 65° C., and rinsing the treated seaweed. Wet treatment steps employ processing liquids with sufficient salt or alcohol to minimize the solubilization and loss of carrageenan during processing. Alcohol washing or ion exchange steps may be employed with compositions and concentrations needed to achieve the desired cation balance of the semi-refined, alkali treated iota carrageenan including use of recycle streams for cost effective operation. The dried powder is further processed to reduce particle size in one or more grinding steps.

The toothpaste composition of the present invention also contains an abrasive, a foaming agent and water.

Abrasives give toothpaste its cleaning power. They remove stains and plaque, as well as polish teeth. Common abrasives include calcium phosphates, alumina, calcium carbonate (chalk) which may be precipitated or natural, and silica. Cellulose particles such as microcrystalline cellulose provide a mild abrasive effect. Toothpaste should be abrasive enough to remove plaque and stains, but not abrasive enough to damage tooth enamel.

Foaming agents create the foaming action commonly associated with toothpastes. Foam assists in removal and suspension of displaced biofilm and food particulates during tooth brushing. Sodium lauryl sulfate (SLS) is a preferred foaming agent.

Other ingredients that may be present can be broadly divided into active ingredients and inactive ingredients as listed below. Active ingredients provide at least one chemical or biological functionality.

Active ingredients include fluoride; antibacterial agents such as triclosan to control plaque; desensitizing agents; anti-tartar agents; sodium bicarbonate (baking soda); enzymes, to enhance the antibacterial properties of saliva; non-sugar sweetener, such as xylitil, which reduces levels of cariogenic (decay causing) bacteria in the mouth; herbal extracts; whitening agents, such as peroxides; functional inclusions or encapsulated functional agents and bioadhesive additives. Fluoride incorporates itself into tooth enamel making the teeth more resistant to acids produced by plaque bacteria, as well as acids found in fruit juices, soda drinks (both regular and diet), and certain foods. In toothpaste, fluoride is in the form of sodium monofluorophosphate, stannous fluoride, or sodium fluoride.

Other ingredients include humectants; flavoring, sweetening, and coloring agents; preservatives; decorative pigments or inclusions; and water.

Humectants give toothpaste its texture and retains moisture so that the toothpaste does not dry out. Glycerin and sorbitol are common humectants. Xylitol is an uncommon, but superior humectant, which also boosts fluoride's cavity fighting power. Water is also a humectant, but is accounted separately.

Other binders may be used in addition to the semi-refined carrageenan, such as other carrageenan, xanthan, carboxymethyl cellulose (CMC), and carbopol. Other thickeners that may be included are bentonite, magnesium aluminum silicate, colloidal grades of microcrystalline cellulose and silica, and sodium alginate. The total amount of all binders may be 0.3 wt. % to 2.0 wt. % of the toothpaste formulations. The semi-refined carrageenan may be present in an amount up to 10% of the total binder by weight; up to 20% of the total binder; between 20% and 50% of the binder; more than 31% of the binder; between 35% to 75% of the binder; more than 50% of the binder; or between 50% to 100% of the binder.

Preservatives prevent the growth of microorganisms in toothpaste which eliminates the need to refrigerate toothpaste. Common preservatives include sodium benzoate, methyl paraben, and ethyl paraben. Flavoring agents such as peppermint, spearmint, cinnamon, wintergreen, and menthol are added to improve the taste of toothpaste and to cover up the taste of most foaming agents, especially SLS. In addition, flavors help create fresh breath and a clean feeling sensation. Sweeteners also improve the taste of toothpaste. Most toothpaste sweeteners are artificial and contribute very little to cavity formation. Saccharin is a common toothpaste sweetener. Coloring agents provide toothpaste with pleasing colors. Artificial dyes and pigments are used to make red, green, and blue toothpastes. Titanium dioxide is used to make some toothpaste white.

After the abrasive, the water, the binder and other ingredients have been accounted for, the humectants account for the balance of material. Typically, as the amount of water is increased, the amount of other humectants in the toothpaste composition decreases. The toothpaste composition typically comprises 8 to 50 weight % of humectants on an absolute basis, i.e., exclusive of any water that is present in the humectants. Sorbitol used as a humectant is, for example, available as 70% sorbitol and 30% water.

The toothpaste composition typically comprises about 0.8 wt % to about 3 wt. %, preferably, about 1% to 2.5 wt. %, of a surface-active foaming agent like SLS. A flavoring agent when present typically comprises about 0.1% to about 2 wt. %, more typically, about 0.5% to about 1.5 wt %. When a sweetener is present, the toothpaste composition typically comprises about 0.1% to about 2 wt. % of the sweetener.

The semi-refined carrageenan can partially or fully substitute for other conventional binders (e.g., refined carrageenans) at typical use levels for such conventional binders (such as 0.3 wt. % to 2.0 wt. %) in order to reduce the costs of such conventional binders.

Toothpaste compositions can be prepared using either the hot process or the ambient process, and either a batch process or a continuous process may be used. The ambient process is sometimes called the cold process. The hot process is described, for example, in Scott, U.S. Pat. No. 4,353,890, and Ballard, U.S. Pat. No. 6,187,293, the disclosures of which are incorporated herein by reference. A continuous process for the manufacture of toothpaste is disclosed, for example, in Ballard, U.S. Pat. No. 6,187,293, the disclosure of which is incorporated herein by reference. A continuous process for the manufacture of toothpaste is also disclosed in Catiis, U.S. Pat. No. 5,236,696.

The disclosure of all references cited herein is incorporated herein by reference, in their entireties.

The present invention is now described in more detail by reference to the following examples, but it should be understood that the invention is not construed as being limited thereto. Unless otherwise indicated herein, all parts, percents, ratios and the like are by weight.

EXAMPLES

The following procedure was used to prepare toothpaste batches under the hot process in order to demonstrate the effectiveness of the polyethylene glycol in improving stability in a toothpaste comprising semi-refined carrageenan. The specific toothpaste formulations tested below were a chalk based toothpaste wherein each binder comprised 36% conventional extract iota carrageenan and 50% semi refined, iota carrageenan. The balance of the binder was silica (14%). The conventional extract iota carrageenan that was used in the testing below was the same and had a viscosity of about 24 cps. The semi-refined carrageenan samples used in the Examples herein were made using similar processes with minor variations and the characteristics of each carrageenan are set forth in the following table. In general, the process that was used was: (a) raw seaweed was washed with an aqueous 1.5 wt % NaCl solution; (b) the seaweed was modified by treating such with an aqueous NaOH and NaCl solution at a temperature of about 45° C.; (c) the seaweed was washed twice at a pH of about 8; (d) the seaweed was then dried and ground to a size as noted in the following Table; and (e) either alcohol washed (three times with increasing amounts of isopropanol) or ion exchanged (in EDTA/NaCl/alcohol) as may be noted in the following Table.

The viscosity of the semi-refined carrageenan was measured using a Brookfield RTV with appropriate speeds and spindles and reported in centipoises (cP). Samples for viscosity testing were prepared by dispersing 7.5 grams of carrageenan powder in 450 grams of deionized water, adding further deionized water to reach 500 grams (net weight), stirring while heating to 85° C., holding for 15 minutes at 85° C., adding back deionized water (as needed) for 1.5% solids, cooling with continuous stirring and testing viscosity when equilibrated at 75° C. Particle size by sieve mesh analysis was determined by adding 50 grams of carrageenan powder sample to the top sieve of a stack of sieves arranged in decreasing mesh size with the coarsest sieve on top and a closed pan on the bottom. The stainless steel sieves are compliant with ASTM standard E-11 specifications with a nominal sieve opening in microns: US #100 (149 microns), and US #230 (63 microns). The covered sieve stack was placed in a Ro-Tap Model RX-29 sieve shaker and the timer was set for 15 minutes. The weight of sample remaining on each sieve was determined and the percentage of powder passing through each sieve was calculated.

Semi-Refined Carrageenan

|  | CGN 1 | CGN 2 | CGN 3 |
|---|---|---|---|
| Alcohol Wash | No | Yes | No |
| pH | 9.9 | 9.5 | 9.6 |
| 100 mesh | 99 | 96 | 96 |
| 230 Mesh | 41 | 27 | 37 |
| Viscosity | 8 | 14 | 13 |
| K | 0.93 | 0.89 | 0.50 |
| Na | 9.98 | 6.39 | 5.37 |
| Na Fraction | 91% | 88% | 91% |

The binder blends used in the toothpastes were as follows.

| Blends Composition Products | Blend 1 % w/w | Blend 2 % w/w | Blend 3 % w/w |
|---|---|---|---|
| Iota Carrageenan | 36 | 36 | 36 |
| CGN 1 | 50 | — | — |
| CGN 2 | — | 50 | — |
| CGN 3 | — | — | 50 |
| Silica | 14 | 14 | 14 |

The details of the tested toothpastes are as follows:

| Ingredients | Amount in Grams |
|---|---|
| Carrageenan Binder Blend | 8.00 |
| Glycerin | 100.00 |
| Sorbitol | 170.00 |
| Saccharin | 2.0 |

| Ingredients | Amount in Grams |
|---|---|
| Sod Benzoate | 3.0 |
| Chalk | 460.0 |
| Flavor | 10.0 |
| SLS | 20.0 |
| Water | 227.0 |
| Total | 1000.0 |

PEG 300 was used in each tested toothpaste in an amount of 2% by weight of the toothpaste composition.

Procedure Used For Making The Toothpaste Tested Herein 8 grams of each carrageenan binder blend was dispersed in to the pre-mixed humectants blend (100 grams Glycerin+170 grams Sorbitol) and stirred for 5 minutes. 227 grams of pre-heated water was added and stirring was continued at 65° C. for 10 mins. 2 grams of saccharin and 3 grams sodium benzoate were added to the elixir and stirring continued at 65° C. for 10 minutes. The above elixir was transferred to a Ross double planetary vacuum mixer equipped with a vacuum Mixer. 460 grams of chalk abrasive were added and mixed well under the vacuum for 15 minutes (Vacuum 760 mm/Hg). 10 grams of flavor was added and mixed well under the vacuum for 10 minutes. 20 grams SLS were added and mixed well under the vacuum for 20 minutes. The batch was discharged for testing and filling.

Testing Procedures

The above toothpaste samples were tested using the following two testing methods.

Toothpaste Viscosity Measurement

The toothpaste viscosity was measured using a Brookfield DV-II+ Viscometer in accordance with the following: Spindle No.: T-E; Spindle Speed: 5 RPM; Temperature: 25 Deg C.; Viscosity Unit: Torque (%) (1%=10,000 centipoises; and Method: Helipath). The toothpaste was squeezed into a 100 ml beaker. The spindle was positioned above the surface of the toothpaste. The spindle was rotated at 5 RPM and the helipath attachment switched on to commence downward movement of the spindle. The viscosity was recorded as soon as the spindle reached 3 cm below the surface of the toothpaste.

Cuban Test

In the Cuban test (also termed the "Rack" test), the paste was squeezed from a tube through a fixed orifice across a grid of parallel rods, increasingly spaced apart. The test results are expressed as the greatest space number (numbers are from 1-12), which represents the longest distance between rods that support the dentifrice ribbon without having it break. The rack was about 300 millimeters (mm) long and about 100 mm wide. The stainless steel rods were spaced at increasing distances apart starting at 3 mm between rods 1 and 2 (space number 1) and the distance between rods increases by 3 mm from rod to rod. Thus, the distance between rods 2 and 3 was 6 mm, and the distance between the twelfth and thirteenth rod (space number 12) was 39 mm. For toothpastes that are not high moisture toothpastes when measured at room temperature, ratings of 1-2 and 9-12 were not acceptable, 3 and 8 were acceptable and 4-7 were good. For toothpastes that are not high moisture toothpastes when measured at 40° C., ratings of 1-2 and 10-12 were not acceptable, 3 and 8-9 were acceptable and 4-7 were good. To carry out the Cuban test, the following procedure was followed. A nozzle was fixed to a toothpaste tube filled with a toothpaste composition to be tested. The tube filled with test toothpaste composition and having the nozzle attached was held at an angle of 45.degree to the rack device. Pressure was applied at the bottom of the tube and a uniform ribbon of paste was squeezed from the tube. While the ribbon of paste was being extruded from the tube the tube was moved across the rack in a straight line. The time to stretch the ribbon of paste over the rack was usually about two to four seconds. If the ribbon breaks before the entire rack was traversed, the procedure was repeated. The ribbon was allowed to stand for 30 seconds. At that time, the point at which the ribbon breaks was recorded as the rack rating or Cuban value. The test was performed five times and the average reading is recorded, rounding off to the nearest complete figure.

Phase Separation in Toothpaste

One of the main forms of instability in toothpaste is known as phase separation. The main indication of phase separation is when the liquid component of toothpaste separates out from the toothpaste ribbon and comes out as oil or water when the paste is squeezed from the tube on the paper. Stability tests were conducted by filling tubes with the sample paste. The tubes were capped and stored flat at room temperature and at 40° C. The test was performed after the 3, 6, 9, 12 week exposure on the samples kept at room temperature and at 40° C. and the observations are recorded each time. A toothpaste ribbon of about 5 cm in length was squeezed from the tube and examined visually. Any occurrence of separate oily phase, water phase or oozing of liquid was considered as a stability defect.

Results

| | CHALK (0-25) TOOTH PASTE INITIAL PROPERTIES, RT AND 40° C. STORAGE TEMPERATURE STABILITY | | | | | |
|---|---|---|---|---|---|---|
| Binder | w/o PEG Blend 1 | w PEG Blend 1 | w/o PEG Blend 2 | w PEG Blend 2 | w/o PEG Blend 3 | w PEG Blend 3 |
| Tooth Paste Viscosity (Next Day) | 27.7 | 22.6 | 28.2 | 21.5 | 22.4 | 21.2 |
| Cuban (Next Day) | 8 | 4 | 9 | 5 | 5 | 4 |
| 40 C. Stability | | | | | | |
| 12 Wks | Sl Fl Sep, Thick | Good | Thick | Good | Good | Good |
| 12 Wks-Cuban | 12 | 9 | 12 | 8 | 6 | 5 |
| 12 Wks-Viscosity | >40 | 34.2 | >40 | 31.8 | 35.9 | 27.1 |
| R.T. Stability | | | | | | |
| 12 Wk | Good | Good | Thick | Good | Sl Fl Sep | Good |
| 12 Wk-Cuban | 8 | 5 | 11 | 5 | 6 | 4 |
| 12 Wk-Viscosity | 36.2 | 22.9 | >40 | 20.1 | >40 | 20.5 |

The foregoing tests demonstrate the improved stability and shelf life of toothpastes of the present invention containing semi-refined carrageenan and polyethylene glycol.

What is claimed is:

1. A toothpaste composition comprising a binder, an abrasive, a foaming agent, water, and polyethylene glycol, wherein said binder comprises semi-refined iota carrageenan, and said polyethylene glycol is present in an amount of from 1-5 wt % and has an average molecular weight of between 150 to 650.

2. The toothpaste composition of claim 1, wherein said polyethylene glycol is present in an amount of 2 wt %.

3. The toothpaste composition of claim 1, wherein said polyethylene glycol has an average molecular weight of between 190 to 210.

4. The toothpaste composition of claim 1, wherein said polyethylene glycol has an average molecular weight of between 285 to 315.

5. The toothpaste composition of claim 1, wherein said polyethylene glycol has an average molecular weight of between 380 to 420.

6. The toothpaste composition of claim 1, wherein said polyethylene glycol has an average molecular weight of between 570 to 630.

* * * * *